(12) United States Patent
Sidebotham (10) Patent No.: US 8,758,345 B2
(45) Date of Patent: Jun. 24, 2014

(54) INTERLOCKING NAIL GEOMETRY AND METHOD OF USE

(76) Inventor: Christopher G. Sidebotham, Mendham, NJ (US)

(*) Notice: Subject to any disclaimer, the term of this patent is extended or adjusted under 35 U.S.C. 154(b) by 1120 days.

(21) Appl. No.: 11/525,361

(22) Filed: Sep. 22, 2006

(65) Prior Publication Data

US 2008/0125818 A1    May 29, 2008

(51) Int. Cl.
*A61B 17/72*    (2006.01)

(52) U.S. Cl.
USPC ............................................ 606/62; 606/64

(58) Field of Classification Search
USPC ................ 606/62, 63, 64, 67, 329, 65, 66, 68
See application file for complete search history.

(56) References Cited

U.S. PATENT DOCUMENTS

| | | | | |
|---|---|---|---|---|
| 4,790,304 A * | 12/1988 | Rosenberg | ................. | 606/916 |
| 4,875,474 A * | 10/1989 | Border | ............................. | 606/63 |
| 5,034,013 A * | 7/1991 | Kyle et al. | ..................... | 606/62 |
| 5,116,335 A * | 5/1992 | Hannon et al. | .................. | 606/62 |
| 5,263,955 A * | 11/1993 | Baumgart et al. | ............. | 606/63 |
| 5,441,500 A * | 8/1995 | Seidel et al. | .................... | 606/67 |
| 5,443,466 A * | 8/1995 | Shah | ................................ | 606/62 |
| 5,489,284 A * | 2/1996 | James et al. | ..................... | 606/62 |
| 5,741,256 A * | 4/1998 | Bresina | ........................... | 606/62 |
| 6,355,069 B1 * | 3/2002 | DeCarlo et al. | ............. | 623/23.26 |
| 6,783,530 B1 * | 8/2004 | Levy | ................................ | 606/63 |
| 7,488,320 B2 * | 2/2009 | Middleton | ...................... | 606/62 |
| 8,435,238 B2 * | 5/2013 | Dejardin | ......................... | 606/62 |
| 2002/0111629 A1 * | 8/2002 | Phillips | ........................... | 606/62 |
| 2006/0084997 A1 * | 4/2006 | Dejardin | ......................... | 606/62 |
| 2006/0173457 A1 * | 8/2006 | Tornier | ............................ | 606/62 |

OTHER PUBLICATIONS

"Locking Intermedullary Nailing with and without Reaming for Open Fractures of the Tibial Shaft," pp. 334-341, Journal of Bone and Joint Surgery, Incorporated, vol. 79-A. No. 3, Mar. 1997, by J.F. Keating et al.

"Angle Stable Locking Reduces Interfragmentary Movements and Promotes Healing After Unreamed Nailing," pp. 2028-2037, Journal of Bone and Joint Surgery, vol. 87-A. No. 9, Sep. 2005, by K. Kasper, et al.

(Continued)

*Primary Examiner* — Jerry Cumberledge
(74) *Attorney, Agent, or Firm* — Ernest D. Buff & Associates, LLC; Ernest D. Buff; Margaret A. LeCroix (57) ABSTRACT

An interlocking nail having an hour-glass geometry is used for repair of bone fractures. The hour-glass interlocking nail includes a proximal section, a mid section, and a distal section. Each section of the hour-glass interlocking nail has a diameter. The proximal and distal sections each have a diameter larger than the mid section so that the interlocking nail has an hour-glass geometry. The hour-glass interlocking nail comprises at least one fixation aperture located within either the proximal or distal section of the hour-glass interlocking nail. Preferably, the fixation aperture has a tapered locking design adapted to receive a screw-cone peg. The hour-glass geometry utilized by the interlocking nail is better suited to address a larger population of bone canal geometries, stressing the fracture site with known values within the healing process and preventing inadvertent perforation of the nail through the cortex of the bone. Hour-glass nail geometry more appropriately distributes stresses and promotes better healing at the bone fracture.

14 Claims, 12 Drawing Sheets

(56) References Cited

OTHER PUBLICATIONS

"Effect of Bone Diameter and Eccentric Loading on Fatigue Life of Cortical Screws Used with Interlocking Nails," pp. 569-573, American Journal of Veterinary Research, vol. 64 No. 5, May 2003, by R. L. Aper et al.

"Use of Veterinary Interlocking Mails for Diaphyseal Fractures in Dogs and Cats: 121 Cases," pp. 8-20, Veterinary Surgery, vol. 32 Issue 1, Jan. 2003, by B. Duhautois.

"Two Techniques for Supplementing Interlocking Nail Repair of Fractures of the Humerus, Femur , and Tibia: Results in 12 Dogs and Cats," pp. 673-680, Veterinary Surgery, vol. 33 Issue 6, Nov. 2004, by R. Basinger et al.

"An in Vitro Biomechanical Study of Bone Plate and Interlocking Nail in a Canine Diaphyseal Femoral Fracture Model," pp. 397-408, Veterinary Surgery, vol. 30 Issue 5, Sep. 2001, by A. Bernarde et al.

"Devices and Methods for Interlocking Surgical Screws and Nails," pp. 17-36, Michigan State University ID 04041 Patent application, Filed Nov. 29, 2005 (not yet published).

* cited by examiner

FIG. 1c External Fixator with Pins

A = Pin Angle [convergent]
B = Pin Location
C = Pin Length

FIG. 1b

Interlocking Nail

Screws

[Prior Art]

FIG. 1a

Screws

Bone Plate

INTERLOCKING NAIL GEOMETRY AND METHOD OF USE

BACKGROUND OF THE INVENTION

1. Field of the Invention

The present invention relates to an improved interlocking nail geometry and method for use; and more particularly to an interlocking nail having an hourglass-shaped construction with an optional self-tapping tapered locking design.

2. Description of the Prior Art

Animals and humans often suffer from long bone fractures, such as fractures of the femur, tibia and humerus, which require medical intervention for stabilization. Surgery is generally required and involves implantation of devices appointed to provide stability for bone healing. Reconstruction of long bone fractures is generally achieved utilizing various implant devices currently available in human and veterinary fields. Varying levels of success are achieved through use of these conventional orthopedic devices based on their ability to stabilize the fracture and promote bone healing.

Non-stability at the fracture site can result in delayed healing and, in some cases, non-union of the fracture, thereby requiring revision surgery. In the latter scenario, fibrous tissue grows at the fracture site instead of bone, creating an unstable, painful limb. Non-union cases require revision surgery using combinations of these devices, i.e., interlocking nails in adjunct with an external fixator device. The common basis for resolving non-stability problems is to establish adequate resistance to bending and torsion through these device reconstructions, thereby preventing excessive motion at the fracture site and allowing the bone to bridge.

Orthopedic devices currently utilized involve combinations of implant devices, including: (i) external fixation devices with pins; (ii) bone plates and screws; and (iii) interlocking nails and transverse bolts or screws. (See FIGS. 1a, 1b, and 1c herein).

External fixation devices frequently fail to provide the requisite stability for proper bone healing, making use of these devices undesirable. Problems with external fixation devices occur not only from stability, but are also due to infection, as the pins used to stabilize the fragments extend through the skin into the bone, resulting in potential pathways for bacteria. Stability can be provided utilizing bone plates and screws, implantation of these devices requires invasive surgical procedures. Interlocking nails heretofore disclosed and utilized provide a less invasive approach than the bone plates and screws. However most designs of these devices do not provide adequate resistance to bending and torsion, and result in delayed union or non-unions due to micromotion of the construct.

Current interlocking nails are inadequate in achieving stability due to the nail geometry and the fit between the screw and the nail. Most nails are a straight rod design of consistent cross section, which creates higher stresses at the proximal and distal portions of the nail challenging the fixation. If these fracture fixation issues can be resolved, interlocking nails have the potential to provide a less invasive surgical approach and yield proper bone stabilization to promote healing.

Notwithstanding the efforts of prior art workers to construct an efficient interlocking nail that stabilizes bone fractures and promotes healing, there remains a need in the art for an interlocking nail having a geometry that promotes stability and, at the same time, requires less invasive surgical implantation. In addition, there is a need in the art for an interlocking nail having an hour-glass geometry and an optional rounded entry tip. Further, there is an art-recognized need for an interlocking nail having an hour-glass geometry and fixation holes provided with a self-tapping, tapered, locking design.

SUMMARY OF THE INVENTION

The present invention provides an interlocking nail having an hour-glass geometry especially suited to stabilize bone fractures and promote healing. An hour-glass geometry is utilized by the interlocking nail to increase stability and provide for flexible entry into bone canals. The hour-glass shape of the interlocking nail permits a less invasive surgical implantation than can be achieved with conventional implantation devices. In addition, the hour-glass shaped interlocking nail contains an optional rounded tip that affords smoother entry of the nail, while minimizing further injury to the bone. Fixation holes are provided within the hour-glass interlocking nail construction. These fixation holes, or apertures, preferably comprise a self-tapping, tapered, locking design.

The hour-glass interlocking nail geometry and method of use provide a novel design for an interlocking nail device. Introduction into the canal of long bones is more readily achieved, thereby minimizing the insertion force. The hour-glass geometry utilized by the hour-glass interlocking nail is better suited to address a larger population of bone canal geometries, stressing the fracture site with known values within the healing process and preventing inadvertent perforation of the nail through the cortex of the bone. Hour-glass nail geometry more appropriately distributes stresses and promotes better healing at the bone fracture. The loading process produced by the hour-glass nail geometry correspondingly results in less stress at the proximal and distal ends and a more biocompatible micromotion at the fracture, which helps to prevent loosening of the implantation device.

The hour-glass interlocking nail includes a proximal section, a mid section, and a distal section. Each section of the hour-glass interlocking nail has a diameter. The proximal and distal sections have diameters larger than the mid section so that the hour-glass interlocking nail has an hour-glass geometry. In addition, the hour-glass interlocking nail comprises at least one fixation aperture located within either the proximal or distal section of the hour-glass interlocking nail.

In one embodiment, the hour-glass interlocking nail's proximal and distal sections each have at least one fixation aperture. Alternatively, the proximal and distal sections of the hour-glass interlocking nail each have two fixation apertures. The fixation aperture may have a first aperture diameter and a second aperture diameter. The first aperture diameter is larger than the second aperture diameter, so that the fixation aperture has a tapered locking mechanism integrated therein. Alternatively, the fixation aperture is adapted to receive a screw, bolt, peg, or the like. The fixation aperture may further comprise grooves therein, appointed to engage with grooves on a screw, bolt, or peg, or the like. The hour-glass interlocking nail may comprise a plurality of fixation apertures located within each of the proximal or distal sections.

In another embodiment the distal section comprises a distal tip having an arc therein constructed to form a tip having at least one arc portion. Alternatively, the distal section comprises a distal tip having a substantially arced tip constructed to form a substantially radiused tip. Optionally the distal section comprises a distal tip having at least one flat edge adapted to form a substantially sharp tip.

The proximal section may comprise a proximal end comprising a connector adapted to be utilized for insertion and alignment of the hour-glass interlocking nail into a bone canal. The connector further comprises at least one ridge portion, at least one cut-out portion, and a central aperture. The central aperture extends through the proximal end and traverses into the proximal section. Optionally, the central aperture is threaded and adapted to receive a bit for insertion and alignment of the hour-glass interlocking nail into the bone canal.

Instead of the connector comprising at least one ridge portion, cut-out portion, and central aperture, the connector may alternatively comprise a conical fitting projecting from the proximal end. The conical fitting may comprise at least one flat side. The conical fitting having the at least one flat side is utilized for positioning and rotational control of the hour-glass interlocking nail during insertion and alignment.

In another embodiment, the proximal section has a proximal diameter, the distal section has a distal diameter, and the mid section has a first, second, and central diameter. The proximal and distal sections each have a diameter larger than the mid section. In turn, the first and second diameters of the mid section are larger than the central diameter of the mid section. The mid section is appointed to flex when the hour-glass interlocking nail is inserted into a bone canal having a curved geometry.

A method of using an hour-glass interlocking nail having an hour-glass geometry is provided. The method comprises the first step of examining a bone fracture to determine an appropriate sized hour-glass interlocking nail to be utilized. Appropriate length and diameter of the hour-glass interlocking nail are determined when selecting the hour-glass interlocking nail. The fractured bone has a bone canal with bone cortex interstitially therein. The method further comprises selecting the hour-glass interlocking nail. The hour-glass interlocking nail comprises a proximal section, mid section, and distal section. Each section of the hour-glass interlocking nail has a diameter and the proximal and distal sections each have a diameter larger than the mid section so that the hour-glass interlocking nail has an hour-glass geometry. At least one fixation aperture is located within either the proximal or distal section of the hour-glass interlocking nail. The proximal section comprises a proximal end having a connector adapted to be utilized for insertion and alignment of the hour-glass interlocking nail into the bone canal.

At least one locking means is selected. The locking means is appointed to be received by the fixation aperture located within either the proximal or distal section of the hour-glass interlocking nail. The locking means comprises a first end, center, and a second end. A substantial portion of the hour-glass interlocking nail is inserted into the bone canal. An alignment device is attached to the connector of the proximal end of the hour-glass interlocking nail. The bone is penetrated with the locking means, causing the locking means to enter the fixation aperture. A first end of the locking means extends from the hour-glass interlocking nail and traverses into the bone cortex. At the same time, the center of the locking means becomes housed within the fixation aperture, and the second end of the locking means extends from the hour-glass interlocking nail and traverses into the bone cortex opposite the first end.

BRIEF DESCRIPTION OF THE DRAWINGS

The invention will be more fully understood and further advantages will become apparent when reference is had to the following detailed description of the preferred embodiments of the invention and the accompanying drawings, in which.

DETAILED DESCRIPTION OF THE INVENTION

The present invention provides an hour-glass interlocking nail geometry and method of use having a novel design for an interlocking nail device. Introduction into the canal of long bones is more readily achieved, thereby minimizing the insertion force. The hour-glass geometry utilized by the hour-glass interlocking nail is better suited to address a larger population of bone canal geometries, stressing the fracture site with known values within the healing process and preventing inadvertent perforation of the nail through the cortex of the bone. Hour-glass nail geometry more appropriately distributes stresses and promotes better healing to the bone fracture. This loading process via the geometry correspondingly results in less stress at the proximal and distal ends, and a more biocompatible micromotion at the fracture helping to prevent loosening of the implantation device. The term ILN, as used herein, refers to interlocking nail. The term HR-ILN, as used herein, refers to the novel hour-glass interlocking nail of the subject invention.

The hour-glass interlocking nail geometry and method of use comprises geometry with an area moment of inertia (AMI) consistent with the AMI of bone plates which have successfully demonstrated the achievement of sufficient stability for fracture fixation. This AMI, relative to the AMI of successful bone plates, is established at the center of the nail and the resulting fracture site. The term AMI, as used herein, refers to the area moment of inertia.

Figure 1A:
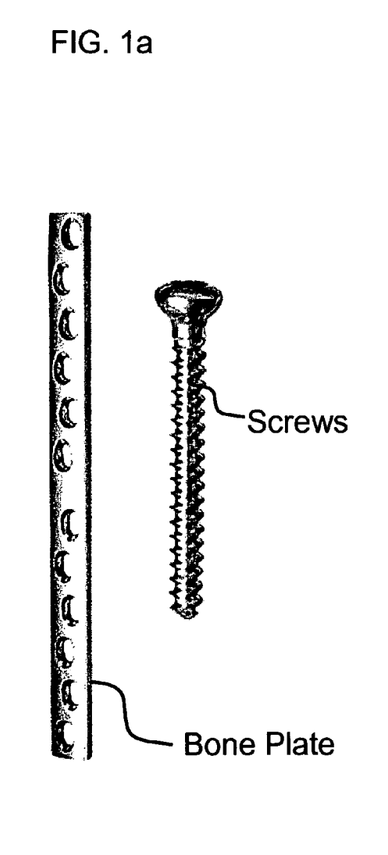
FIGS. 1a, 1b, and 1c illustrate fractional fixation devices currently used in human and veterinary orthopedics.
Figure 1B:
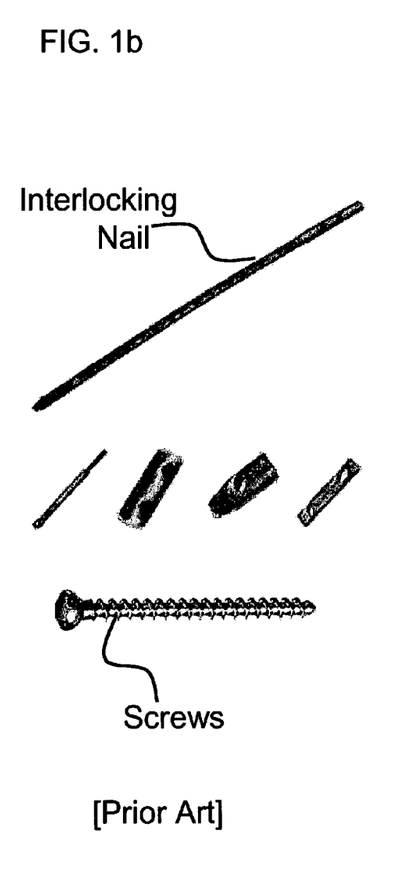
Figure 1C:
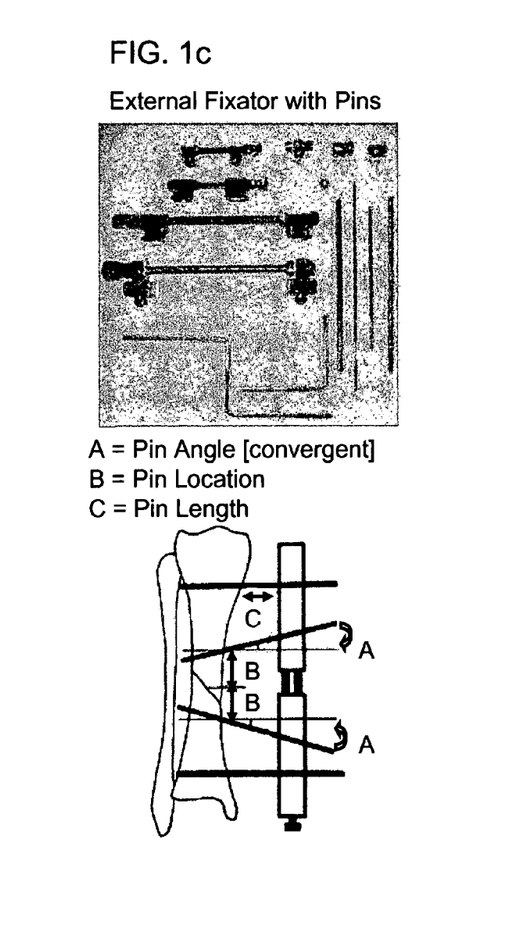

FIGS. 1a, 1b, and 1c illustrate fractional fixation devices currently used in human and veterinary orthopedics. Specifically, FIG. 1a shows a top view of a bone plate and screw combination currently utilized to repair bone fractures; FIG. 1b shows currently utilized interlocking nails and transverse bolts or screws; and FIG. 1c shows currently utilized external fixation devices with pins. These orthopedic devices are currently utilized to repair bone fractures. As set forth hereinabove in the "Description of Prior Art Section", these devices have several disadvantageous. Including, failing to provide the requisite stability for optimal bone healing and frequency in non-union cases, and thereby requiring revision surgery. Plate and screw combinations currently utilized result in invasive surgical procedures, which can increase the patient's healing time as well as risk of infection during the operating procedure. External fixation devices frequently fail to provide the requisite stability and also can lead to infection as the pins used to stabilize the fragments extend through the skin into the bone, resulting in potential pathways for bacteria. Interlocking nails currently utilized provide a less invasive approach than the bone plates and screws, however most designs of these devices do not provide adequate resistance to bending and torsion and result in delayed union or non-unions due to micro motion of the construct.

Figure 2A:
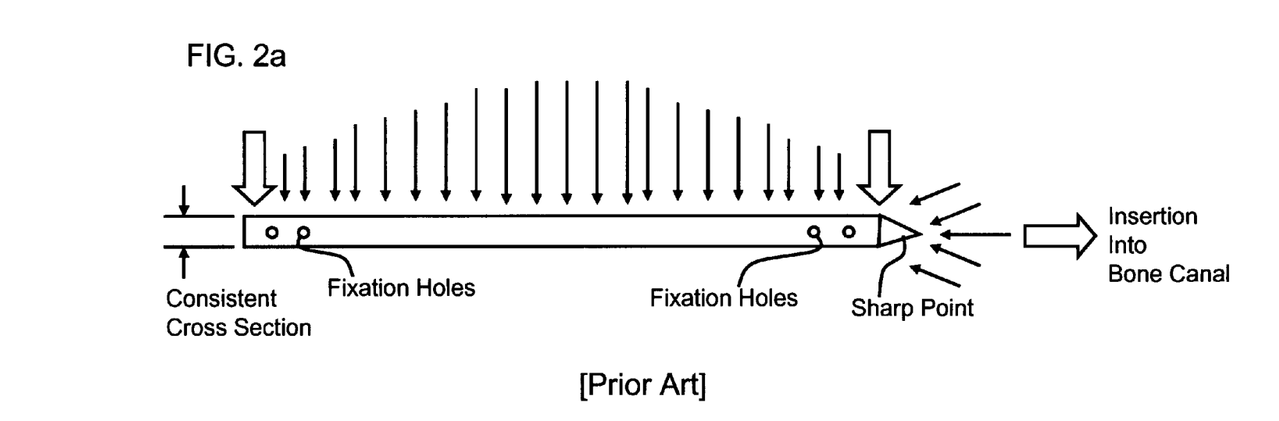
FIGS. 2a and 2b illustrate conventional interlocking nails having straight nail rigid geometries and sharp point constructions, and further illustrate stress distribution and disadvantageous of the combination of straight nail geometry and sharp point construction during insertion of the interlocking nail into a bone canal.
Figure 2B:
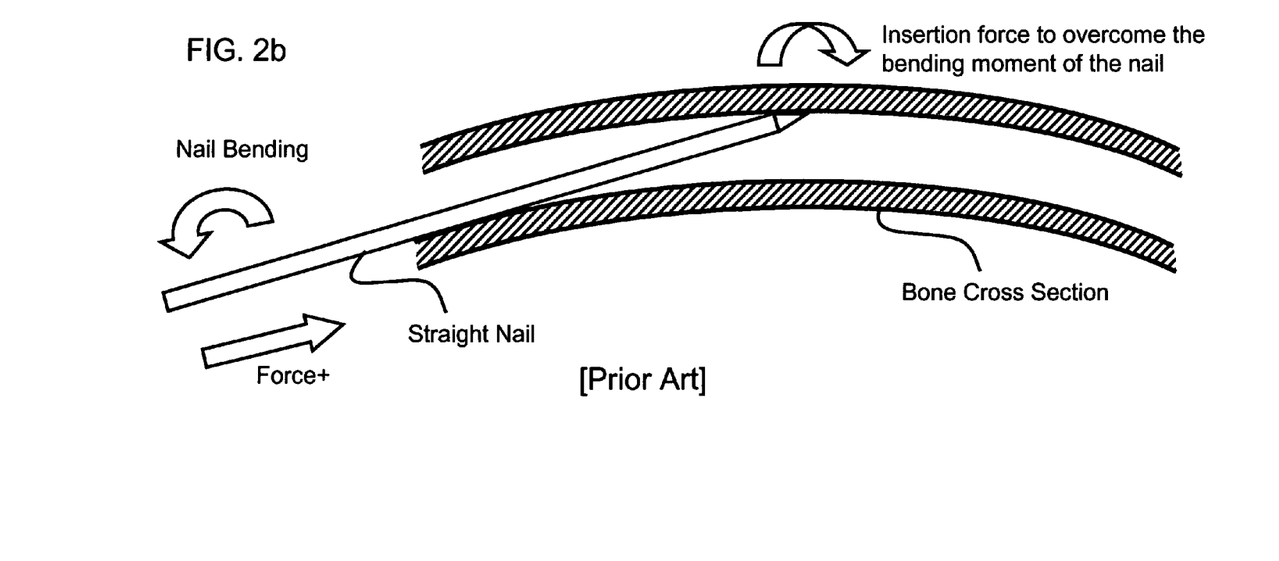

FIGS. 2a and 2b illustrate conventionally utilized interlocking nails having straight nail rigid geometry and sharp point construction, and further illustrate stress distribution and disadvantageous of the combination of straight nail geometry and sharp point construction during insertion of the interlocking nail into a bone canal. FIG. 2a shows a side view of a conventional interlocking nail; FIG. 2b shows insertion of the conventional interlocking nail into a bone cavity. Conventional interlocking nails generally have a rigid straight construction appointed with a sharp point and fixation holes. Current interlocking nails are inadequate in achieving stability due to the nail geometry and the fit between the screw and the nail. Most nails are a straight rod design of consistent cross section, which creates higher stresses at the proximal and distal portions of the nail, challenging fixation and interrupting bone healing. If these fixation issues can be resolved, interlocking nails have the potential to provide a less invasive surgical approach and yield proper bone stabilization to promote healing. Flexible interlocking nail geometry is also important to the reconstruction of a fractured bone. Insertion force must be applied to overcome the bending moment of the nail. During insertion into curved long bones, stiffer nail designs resist adequate flexing. As a result, the fractured bone is forced to conform to the nail's geometry rather than the nail conform to the bone's geometry. Sharp tips utilized by conventional interlocking nails create high stress to the fractured bone and can perforate the cortex during insertion.

Figure 3:
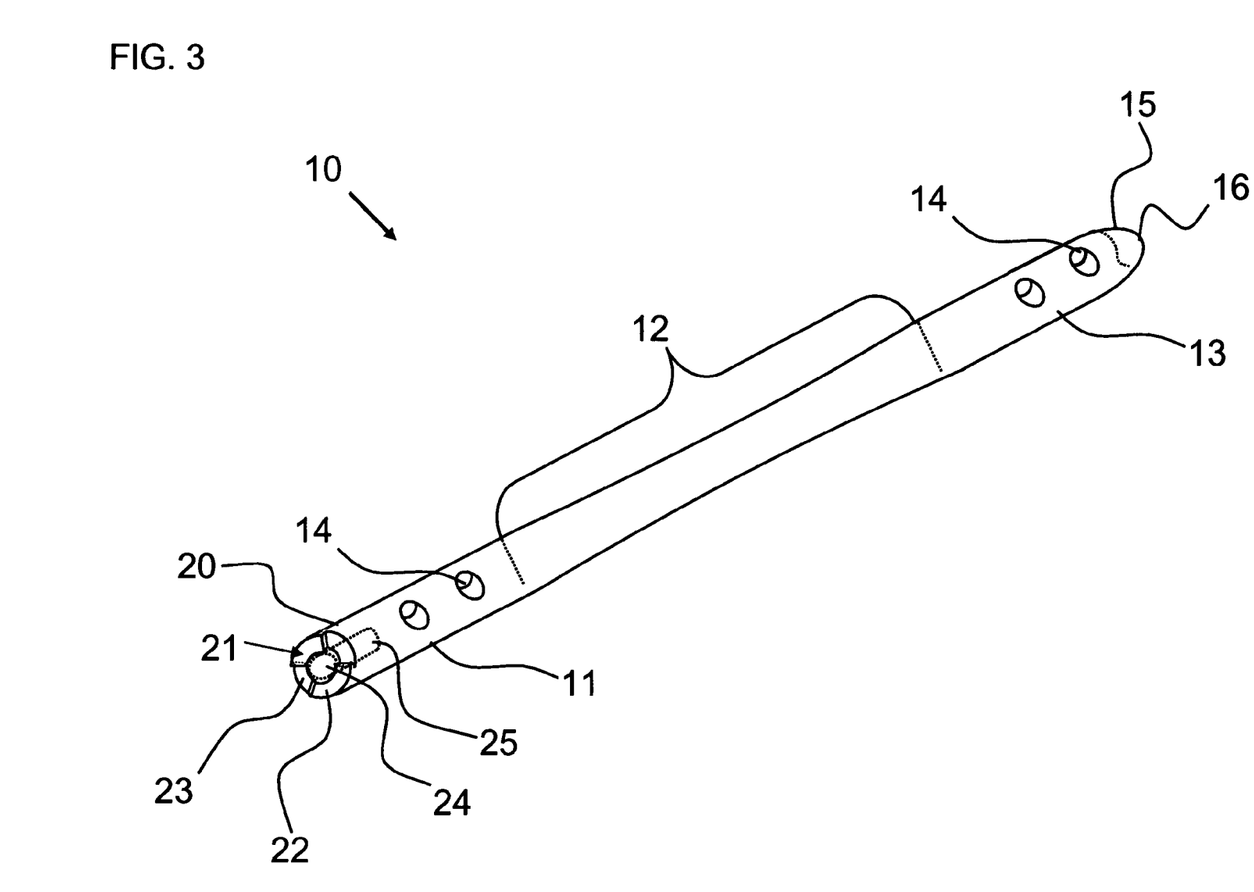
FIG. 3 illustrates a top planer view of the hour-glass interlocking nail geometry of the subject invention.
Figure 4A:
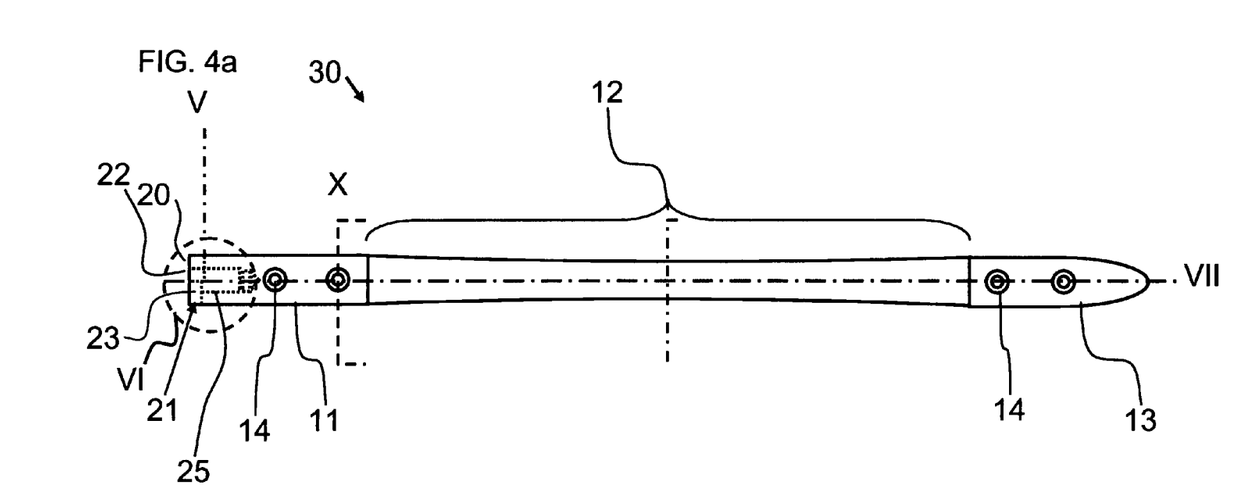
FIGS. 4a, 4b, 4c, and 4d illustrate the hour-glass interlocking nail having a non-rigid geometry with rounded tip construction and self-tapping tapered locking design.

FIG. 3 illustrates a top planer view of the hour-glass interlocking nail geometry of the subject invention, wherein the hour-glass interlocking nail has a non-rigid geometry and rounded tip construction and self-tapping tapered locking design shown generally at 10. FIG. 4a illustrates a side view of the hour-glass interlocking nail having a non-rigid geometry and rounded tip construction and self-tapping tapered locking design, shown generally at 30. Hour-glass interlocking nail 10, 30 comprises a proximal section 11, mid section 12, and distal section 13. Each section, 11, 12, and 13 of the hour-glass interlocking nail has a diameter. The proximal and distal sections, 11 and 13, each have a diameter larger than the mid section 12 so that the hour-glass interlocking nail has hour-glass geometry.

Hour-glass interlocking nail 10, 30 comprises at least one fixation aperture 14 located within either the proximal or distal section, 11, 13. Preferably, fixation aperture 14 is tapered and has a locking design (discussed hereinafter). In one embodiment the hour-glass interlocking nail's proximal and distal sections, 11, and 13, each have at least one fixation aperture 14. Preferably the hour-glass interlocking nail 10, 30, comprises a plurality of fixation apertures 14 located within each of the proximal and l or distal sections 11, 13, and l or throughout the mid section 11 (See FIG. 10 herein showing an alternative embodiment of FIG. 6b). Most preferably, the proximal and distal sections, 11 and 13, of the hour-glass interlocking nail each have two fixation apertures, as is shown in FIGS. 3 and 4a.

Proximal section 11 comprises a proximal end 20 having a connector 21 constructed interstitially therein. Connector 21 is appointed to be utilized for insertion and alignment of the hour-glass interlocking nail into a bone canal. In the embodiment shown in FIGS. 4a-4d, connector 20 further comprises at least one ridge portion 22, at least one cut-out portion 23, and a central aperture 24. Central aperture 24 extends through proximal end 20 and traverses into proximal section 11, forming a central cavity 25. Optionally, central cavity 25 is threaded or grooved and is appointed to receive a bit for insertion and alignment of the hour-glass interlocking nail into the bone canal. (Discussed in further detail via FIGS. 4c and 4d). Instead of the connector comprising at least one ridge portion, cut-out portion, and central aperture, the connector may alternatively comprise a conical fitting projecting from the proximal end. This alternative embodiment is shown in FIGS. 5a and 5b and same is discussed hereinbelow.

Figure 4B:
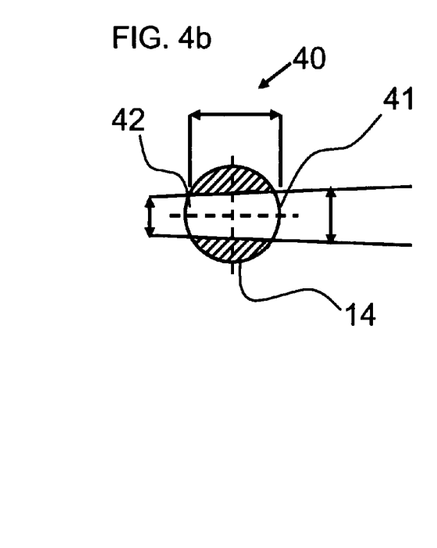
Figure 5A:
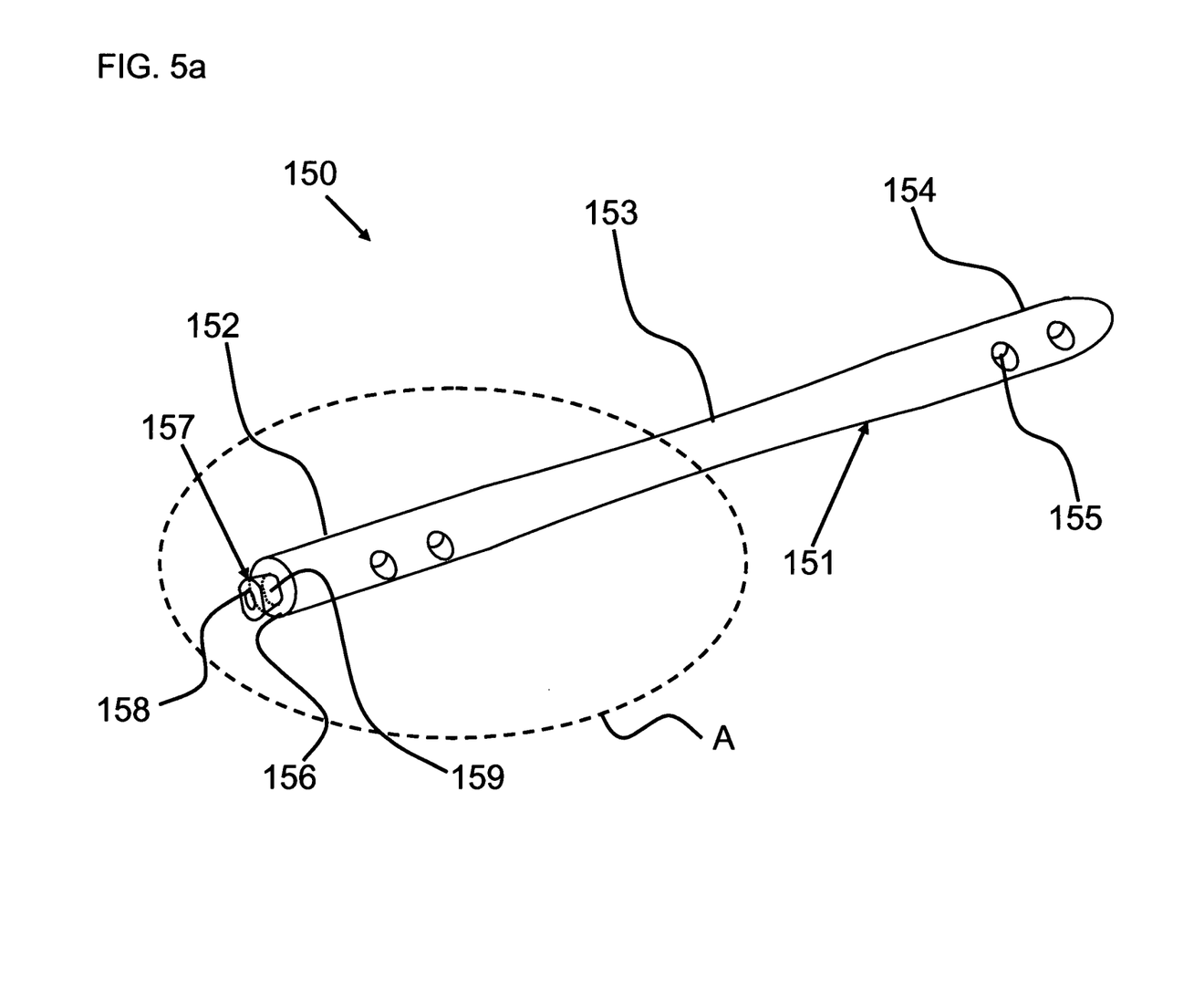
FIGS. 5a and 5b illustrate views of the hour-glass interlocking nail having a non-rigid geometry and rounded tip construction, and further illustrate an alternative embodiment wherein the connector comprises a conical fitting projecting from the proximal end.
Figure 5B:
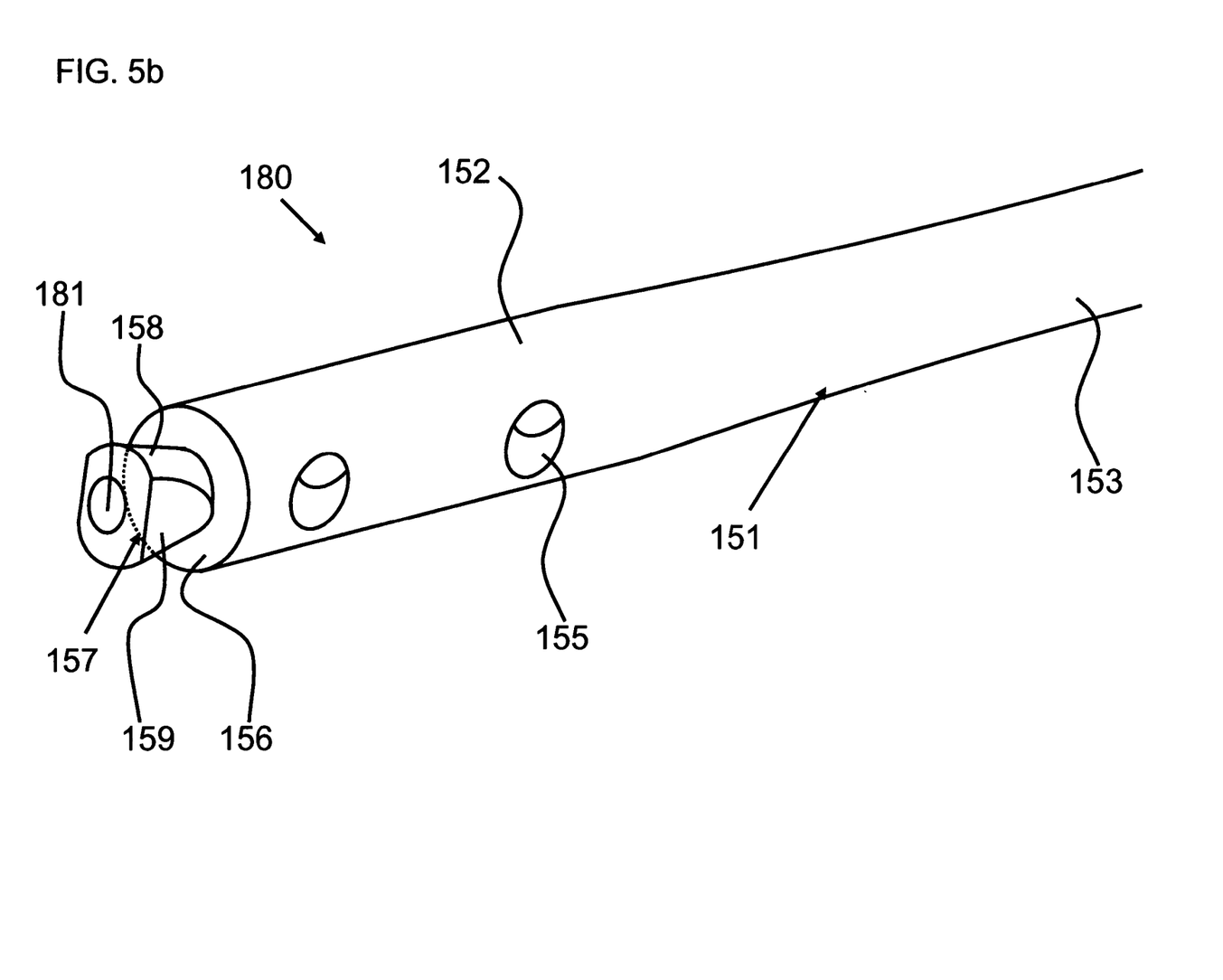

FIG. 4b illustrates a cross-sectional view of a preferred embodiment of the fixation aperture taken along line X of FIG. 4a, wherein the fixation aperture comprises a self-tapping tapered locking design, shown generally at 40. As best illustrated in FIG. 4b, fixation aperture 14 has a first aperture diameter 41 and a second aperture diameter 42. First aperture diameter 41 is larger than second aperture diameter 42 so that the fixation aperture 14 has a tapered configuration. This tapered configuration is integrated within the hour-glass interlocking nail 30 and acts as a locking mechanism for securing the hour-glass interlocking nail to the bone cortex. Fixation aperture 14 is appointed to receive a tapered screw, screw-cone peg locking device, screw, bolt, peg, or the like for fixture of the hour-glass interlocking nail within the bone. The fixation aperture 14 may further comprise grooves therein, appointed to engage with grooves on a screw-cone peg, screw, bolt, or peg, or the like for fixture of the hour-glass interlocking nail within the bone.

Continuing with FIGS. 1 and 4a, distal section 13 comprises a distal tip 15. Distal tip 15 may have at least one flat edge to form a substantially sharp tip (shown in FIG. 8). Preferably, distal tip 15 is appointed with an arc therein constructed to form a tip having at least one arc portion so that the distal tip 15 has a rounded portion constructed therein. Most preferably, distal tip 15 has a substantially arced or rounded tip therein constructed to form a substantially radiused or semi-spherical bullet point tip 16. (See FIGS. 6a, 6b, and 6c).

Proximal section 11 comprises a proximal end 20 having a connector 21 constructed interstitially therein. Connector 21 is appointed to be utilized for insertion and alignment of the hour-glass interlocking nail into a bone canal. In the embodiment shown in FIGS. 4a-4d connector 20 further comprises at least one ridge portion 22, at least one cut-out portion 23, and a central aperture 24. Central aperture 24 extends through proximal end 20 and traverses into proximal section 11, forming a central cavity 25. Optionally, central cavity 25 is threaded or grooved and is appointed to receive a bit for insertion and alignment of the hour-glass interlocking nail into the bone canal. Instead, the connector may alternatively comprise a conical fitting projecting from the proximal end.

This alternative embodiment is shown in FIGS. 5a and 5b and same is discussed hereinbelow.

Figure 4C:
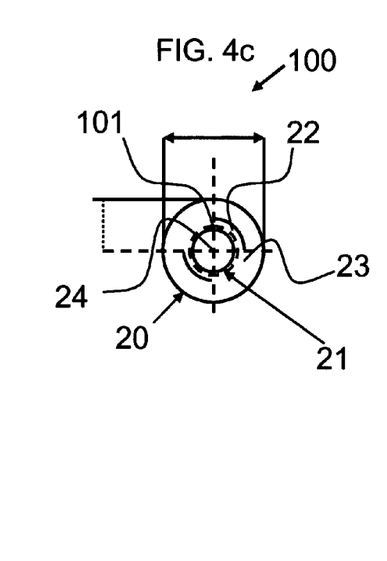
Figure 4D:
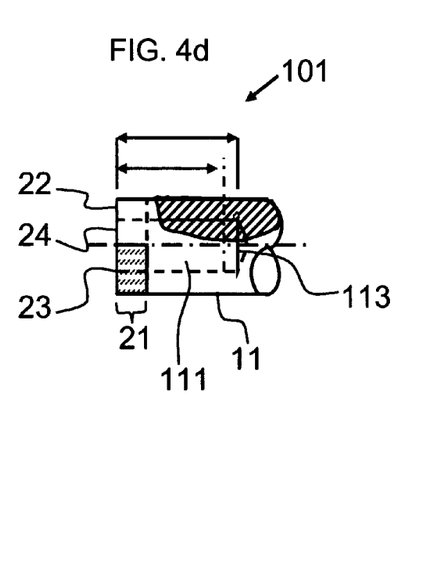

FIGS. 4c and 4d illustrate cross-sectional views of the proximal end 20 and connector 21. FIG. 4c shows the proximal end 20 and connector 21 taken along line V, shown generally at 100. FIG. 4d shows the proximal end 20 and connector 21 taken along section VI and line VII, shown generally at 110. Proximal end 20 is provided with connector 21. As shown in the embodiment of FIG. 4c, proximal end 20 is equipped with connector 21, which has at least one ridge portion 22 and at least one cut-out portion 23. Preferably, there are two ridge portions 22 and two cut-out portions 23 arranged in a staggered arrangement to one another to form a central aperture 24 as is shown in FIG. 4c. Threads or other locking means 101 may be provided within central aperture 24. Referring to FIG. 4d, showing a cross-section side view of the proximal section 11, proximal end 20, and connector 21, central aperture 24 extends within proximal section 11. Preferably, central aperture 24 is fully threaded throughout a body portion 111 of the central aperture 24 to form central cavity 25. Central cavity 25 further includes a central tip 112 and an end tip 113. Preferably, central tip 112 and end tip 113 are not threaded. These ridge portions 22, cut-out portions 23, and central aperture are appointed to engage with a bit, or the like, of an alignment and/or insertion instrument. An alternative embodiment of the connector is shown in FIGS. 5a and 5b and same is discussed hereinbelow.

FIGS. 5a and 5b illustrate views of the hour-glass interlocking nail having a non-rigid geometry and rounded tip construction, and further illustrate an alternative embodiment wherein the connector comprises a conical fitting projecting from the proximal end, shown generally at 150 and 180, respectively. FIG. 5b is shown at 180 and is taken along section A of FIG. 5a. In this embodiment, hour-glass interlocking nail 151 comprises a proximal section 152, mid section 153, and distal section 154. Each section, 152, 153, and 154 of the hour-glass interlocking nail has a diameter. The proximal and distal sections, 152 and 154, each have a diameter larger than the mid section 153 so that the hour-glass interlocking nail has hour-glass geometry. Hour-glass interlocking nail 151 comprises at least one fixation aperture 155 located within either the proximal or distal section, 152, 154. Preferably, fixation aperture 155 is tapered and has a locking design (discussed hereinafter). In one embodiment the hour-glass interlocking nail's proximal and distal sections, 152, and 154, each have at least one fixation aperture 155. Preferably the hour-glass interlocking nail 151 comprises a plurality of fixation apertures 155 located within each of the proximal and/or distal sections 152, 154, and/or throughout the mid section 153. Most preferably, the proximal and distal sections, 152 and 154, of the hour-glass interlocking nail 151 each have two fixation apertures as is shown.

Proximal section 152 comprises a proximal end 156 having a connector 157 constructed interstitially therein. Connector 157 is appointed to be utilized for insertion and alignment of the hour-glass interlocking nail 151 into a bone canal. In the embodiment shown, connector 157 further comprises a conical fitting 158 projecting or outwardly extending from proximal end 156. In this embodiment, connector 157 is appointed to be received in an orifice or aperture of an instrument appointed for aligning and inserting the hour-glass nail 151 into the bone canal. Conical fitting 158 may comprise at least one flat side 159 for advancing positioning and rotational control of the hour-glass interlocking nail during insertion and alignment into the bone canal. Preferably, conical fitting 158 comprises two flat sides 159 arranged parallel to one another. The conical fitting 158 may be threaded for attachment to an alignment/inserter. The connector 157 is conical for locking to the alignment and/insertion instrument and has the side flats for positioning and rotational control during insertion. An indent 181 (shown in FIG. 5b) may be included on conical fitting 158 for further facilitating placement within an insertion or aligning instrument.

Figure 6A:
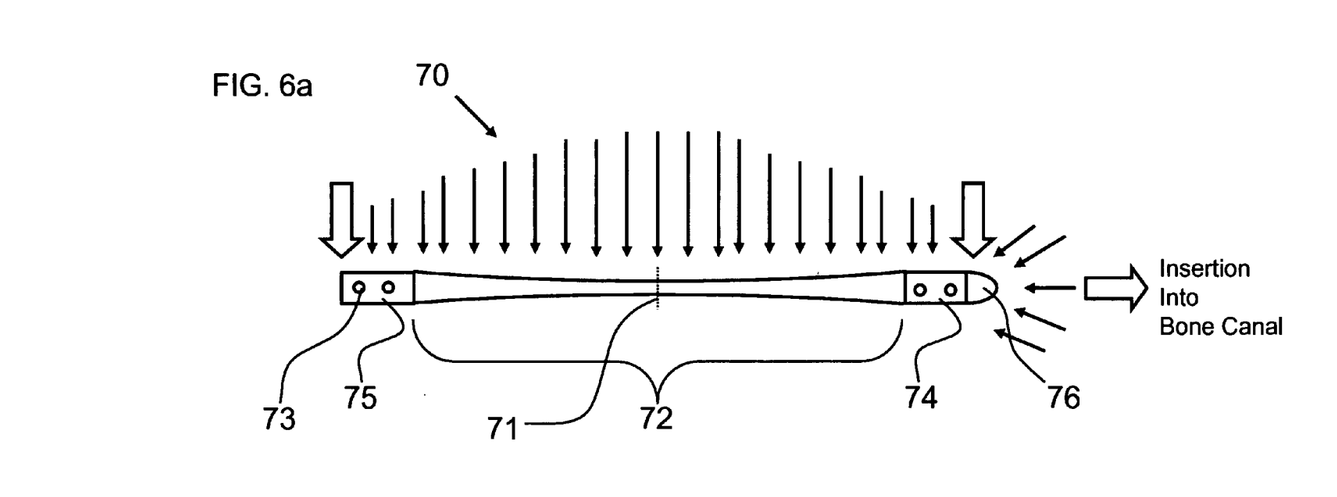
FIGS. 6a, 6b, and 6c illustrate side views of the hour-glass interlocking nail having a non-rigid geometry and rounded tip construction, and further illustrate stress distribution and advantages of the hour-glass interlocking nail geometry during insertion of the interlocking nail into a bone canal.
Figure 6B:
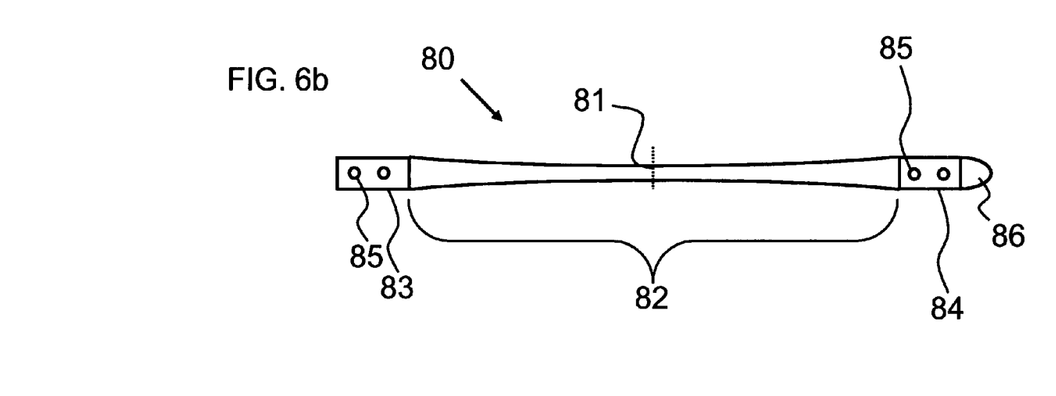
Figure 6C:
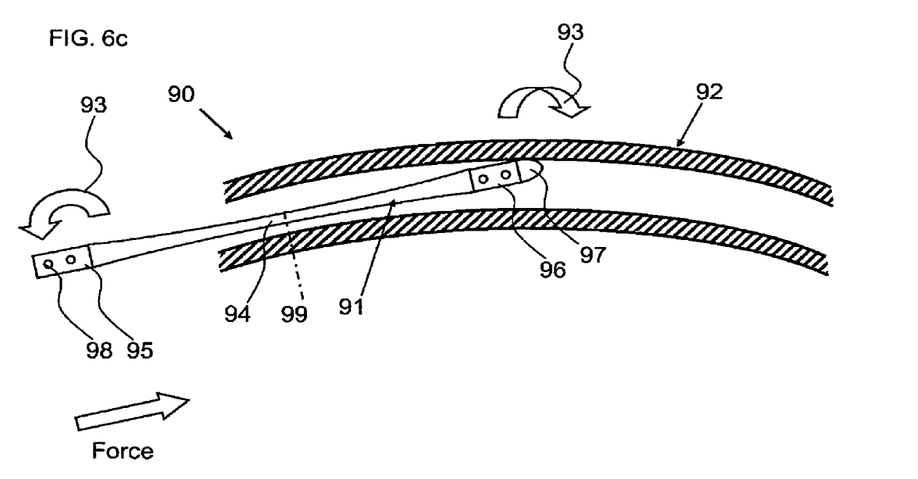

FIGS. 6a, 6b, and 6c illustrate side views of the hour-glass interlocking nail having a non-rigid geometry and rounded tip construction. Specifically, FIG. 6a shows a side view of the hour-glass interlocking nail, illustrating stress distribution, radiused or semi-spherical bullet point tip, and hour-glass construction, shown generally at 70; FIG. 6b shows a side view of the hour-glass interlocking nail wherein the nail has a narrower mid section 12, shown generally at 80; and FIG. 6c shows advantages of the hour-glass interlocking nail geometry during insertion of the interlocking nail into a bone canal, shown generally at 90. Taken from the center 71 of mid section 72, the geometry of the nail 70 gradually increases extending from both sides until establishing two larger diameters at the proximal section 73 and distal section 74 provided with fixation apertures 75. Proximal section 73 has a proximal diameter, the distal section 74 has a distal diameter, and the mid section has a first, second, and central diameter. The proximal and distal sections 73, 74 each have a diameter larger than the mid section 72. The mid section is adapted to flex when the hour-glass interlocking nail is inserted into a bone canal having a curved geometry.

Distal section 74 is provided with a substantially radiused bullet point tip 76. This hour-glass geometry can be accomplished through a large radius or by tapering the nail from the center 71 out to larger proximal and distal sections. Proximal and distal sections are adapted to incorporate screw or bolt holes proving a method of locking the nail to the proximal and distal areas of the bone relative to the fracture site. FIG. 6b shows a more narrowed center 81 of mid section 82 so that there are virtually tapered cones on both sides of the center 81, increasing in radius on both sides to form proximal and distal sections, 83 and 84, and yield hour-glass geometry. Proximal and distal sections 83, 84 are provided with fixation apertures 85. Distal section 84 is provided with a substantially radiused bullet point tip 86.

Hour-glass geometry of the interlocking nail and the designed bullet point promote optimal insertion into the bone canal. Insertion into the bone canal can be achieved without reaming, providing for a less invasive surgical procedure. The use of thinner interlocking nails without reaming of the medullary cavity has biological advantages, such as preservation of the endosteal and medullary blood supply; however, thin INLs procedure places the construct at a mechanical disadvantage by reducing the nail-bone contact area and increasing the working length of the locking device. The HR-INL provides the ability to reduce the need for reaming, while at the same time aids in preserving the endosteal and medullary blood supply within the bone. See FIG. 6c. Bullet point tip (semi-spherical) construction at the end of the distal section also provides an insurance against inadvertent perforation of the bone canal during insertion, as is often seen with traditional sharp point interlocking nail tips. (Compare FIGS. 2b and 6c).

The geometry of the hour-glass ILN (HR-ILN) conforms to the natural geometry of the internal canal of bones and promotes bone healing. Insertion of the nail is also improved through the hour-glass geometry by allowing the nail to better flex at its center point 99 in length (FIG. 6c). FIG. 6c shows insertion of the interlocking nail into a bone canal at 90. Force is applied as HR-ILN 91 is inserted into a bone canal 92, HR-ILN 91 bends or flexes as indicated by arrows 93 at center point 99. FIG. 6c illustrates the geometry of the hour-glass nail during insertion. HR-ILN 91 includes mid section 94 with narrow center point 99, proximal section 95, and distal section 96 baying radiused bullet tip 97. Fixation apertures 98 are provided. The narrow diameter of mid section 94 at center point 99 facilitates bending of the HR-ILN 91 so that the nail can flex to insert into curved geometry of bone canal 92 with less stress to the bone and the HR-MN 91.

Conventional nails' consistent diameters create additional required insertion loads to overcome the bending stresses due to the curvature of the bone canal. As a result, greater force must be applied when insertion of the conventional nail is required. Reaming is often required when utilizing the conventional interlocking nail. The hour-glass geometry of the novel interlocking nail herein provides benefit of insertion with less necessity for reaming. At the same time, the hour-glass geometry provides ease of insertion into the bone canal, and can minimize the pressure to the endosteum and improve the re-establishment of the medullary blood supply. These features can enhance the bone healing process. The HR-ILN geometry also provides a more balanced stress distribution to the bone. Fixation is achieved through the screws or bolts in the proximal and distal sections of the nail for bone attachment. In a straight consistent cross sectional nail, these ends are exposed to higher stresses and therefore challenge the fixation of the nail to the bone from inception.

The hour-glass geometry re-directs these stresses to the fracture site, which is still capable of resisting deflection and excess micro motion based on the AMI of the center section. Transferring these stresses, minimizes the stress to the fixation ends thereby providing for a more designed stress distribution capable of better fixation and fracture healing. The basic shape of the hour-glass also eliminates any abrupt changes in geometry which would be seen from a geometry providing larger ends for fixation with a reduced center section to the nail.

Figure 7:
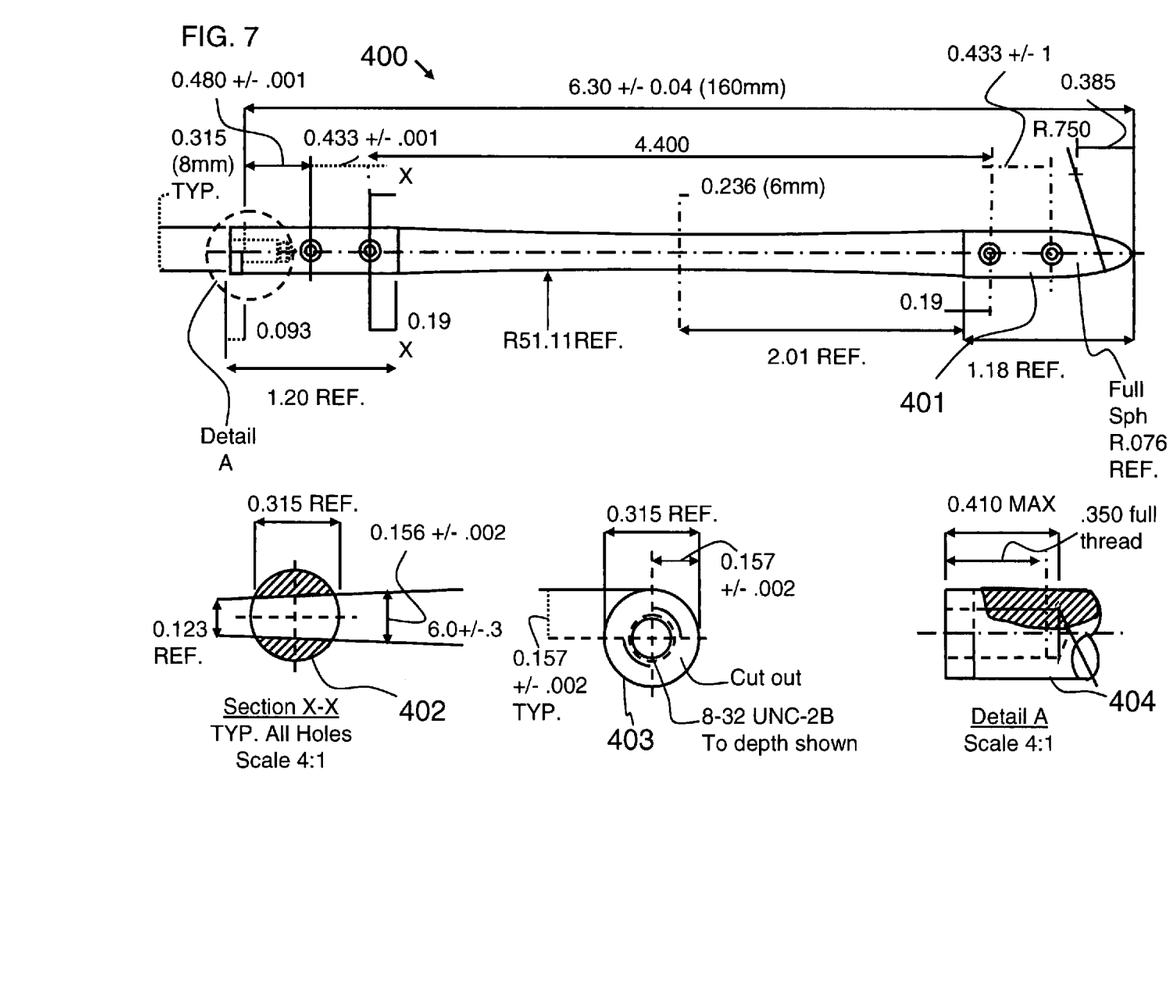
FIG. 7 illustrates the hour-glass interlocking nail shown in FIGS. 4a-4d having a non-rigid geometry with rounded tip construction and self-tapping tapered locking design, illustrating mechanical measurements for a 160 mm nail.

FIG. 7 illustrates the hour-glass interlocking nail shown in FIGS. 4a-4d having a non-rigid geometry with rounded tip construction and self-tapping tapered locking design, illustrating mechanical measurements for a 160 mm nail, shown generally at 400. The hour-glass interlocking nail has a rounded tip 401. Tapered locking design of the fixation aperture is shown at 402, and the embodiment of the connector having at least one ridge portion (preferably at least two) and at least one cut-out portion (preferably at least two) as illustrated in FIGS. 4a-4d is shown at 403 and 404.

Figure 8:
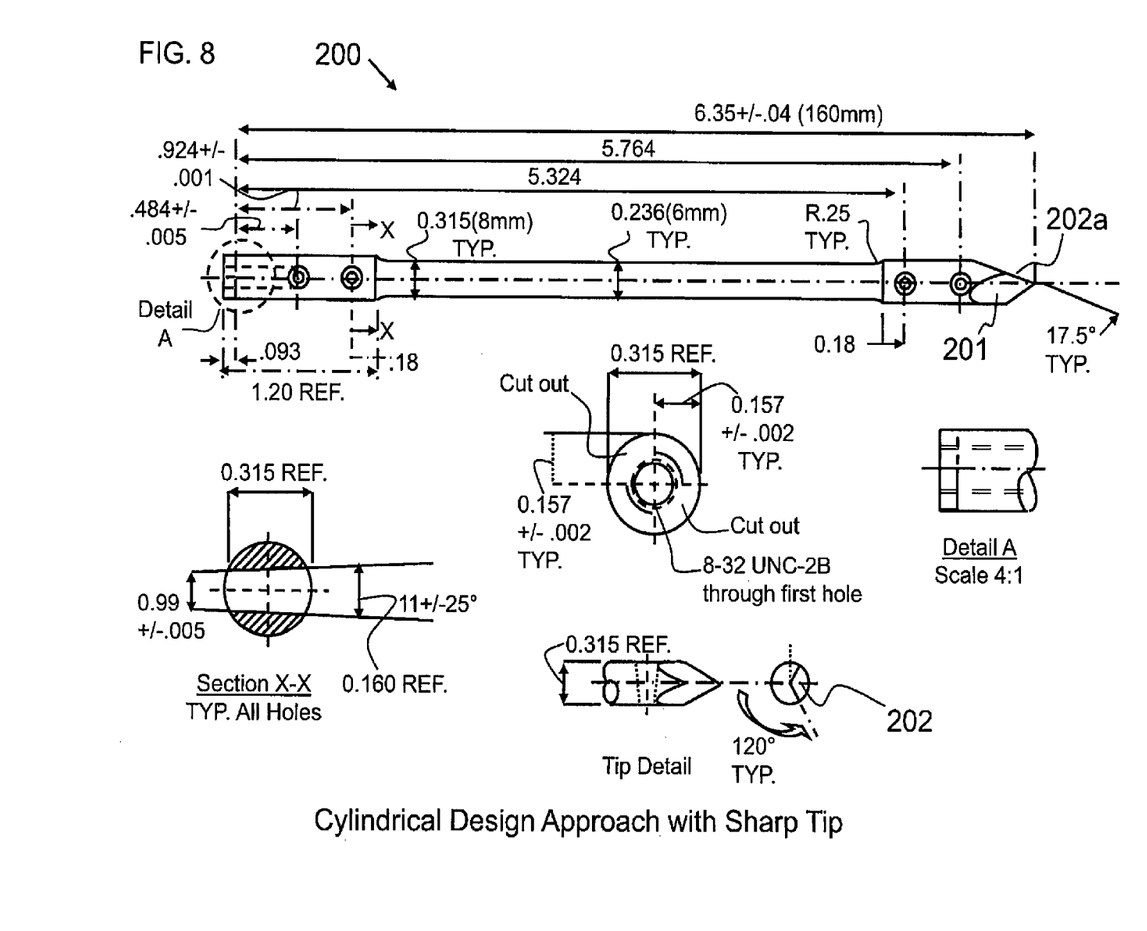
FIG. 8 illustrates a side view of another embodiment or derivation of the hour-glass interlocking nail of the current invention, showing a reduced mid-section or sharp point design embodiment.
Figure 9:
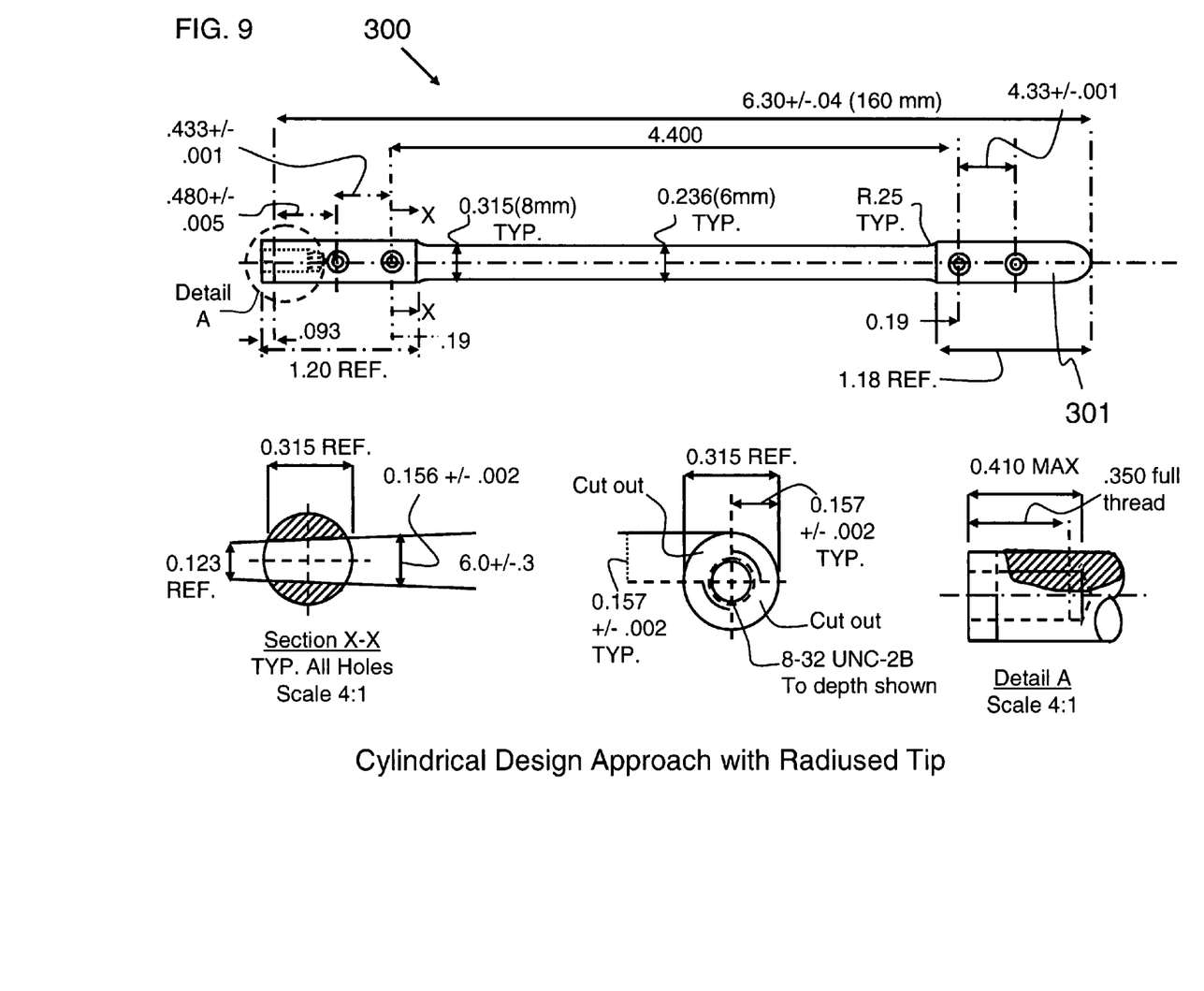
FIG. 9 illustrates a side view of another embodiment or derivation of the-hour-glass interlocking nail of the current invention, showing a reduced section or-rounded/radiused tip design.

FIGS. 8 and 9 illustrate side views of derivations of the hour-glass interlocking nail of the current invention. Specifically, these figures show a less gradual indentation. FIG. 8 shows a reduced mid-section or sharp point design embodiment, shown generally at 200. A view of the tapered fixation aperture is also shown, along with views of the connector and tip detail. Herein, the distal end has a pointed or sharp point design tip 201. Sharp tip 201 has at least one flat edge 202a to form a substantially sharp tip. Herein, sharp tip 201 has three flat sides to form a pyramidal sharp tip shown at 202. FIG. 9 shows a reduced mid-section or rounded or bullet point design 301 embodiment, shown generally at 300. FIGS. 8 and 9 are drawings of similar devices but without encompassing all the benefits of the hour-glass geometry. Although the cross section of the hour-glass ILN is shown as a circle, it is also envisioned that different cross sections such as a "Y" or an "X" could provide similar benefits in an hour-glass nail geometry. Initial stability of the hour-glass nail can be achieved through the fixation apertures in the larger diameter cylinders at each end (proximal and distal sections). These fixation apertures can be designed to accept screws, bolts, screw-cone pegs, threaded or non-threaded with the intent of solid fixation to the nail and fixation to the cortices of the bone. This secured fixation between the nail and the bone provides the opportunity for the nail geometry to afford the proper biomechanics for fracture fixation.

Clinical observation was done utilizing 8-mm ILN (hereinafter, ILN8) to treat comminuted fractures of the tibial diaphysis in dogs of mixed-breed, weighing approximately 30 to 35 kg. Prototypes of the HR-ILN (hour-glass interlocking nail of the present invention) system were designed to be of a size comparable to commercially available 8×185-mm ILN. Several primary constraints were addressed in designing the HR-ILN prototypes, including: providing a rigid interaction between the bone and the HR-ILN; and providing a shape that would limit interference with endocortices and facilitate fracture reduction while limiting the risk of joint infraction attributed to perforation of the implant device. In addition, the shape and size of the novel HR-ILN addressed surgical insertion constraints, making insertion easier while mitigating the need for reaming.

The prototypical HR-ILN further addresses secondary constraints of current ILNs, including stiffness and strength issues. The HR-ILN includes a locking device that provides rigid interaction with the nail via tapered fixation apertures, as well as the connector adapted to ensure proper alignment and insertion of the fixation means (i.e. screws, etc.). The AMI of the HR-WLN is greater than that of a 45-mm bone screw and comparable to that of a commercially available 3.5-mm locking bolt. The fixation hole or aperture was designed to be similar to an ILN8 with 3.5-mm bone screws. Prototypes of the HR-ILN were developed having the hour-glass shaped nail featuring an oblong bullet like distal tip and a screw-cone peg locking device. Manufacture of the prototypes was from 316L stainless-steel certified to ASTM F138 standards. The material was chosen because it is the current material of choice for medical manufacturers of similar implants. The patent contemplates use of any suitable material. The outside diameter of the nail ends (proximal and distal) was 8 mm and the center of the mid section was 6 mm at is center. Each proximal and distal section of the nail included two fixation holes, tapered and having a diameter of 40 and 32, respectively. The tapered fixation holes were placed 11 mm apart in each end of the nail. The most proximal and distal nail holes were separated by 155.5 mm. The screw-cone peg was designed as a self-tapping, cortical-type screw with a central Morse taper that corresponded to the fixation holes or apertures. The core diameter of the screw-cone peg was 4 mm and was manufactured in tow lengths, 26 and 30 mm.

Figure 10:
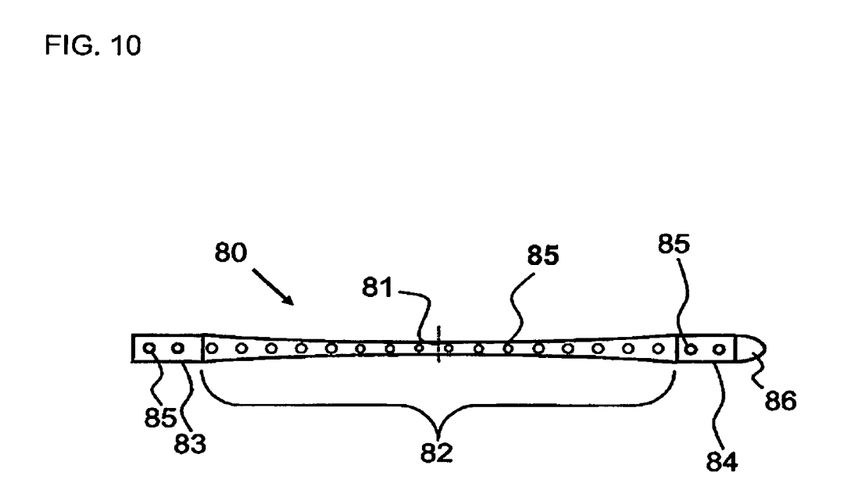
FIG. 10 illustrates an alternative embodiment of the hour-glass interlocking nail of FIG. 6b wherein a plurality of fixation apertures is located throughout the mid section.

FIG. 10 illustrates an alternative embodiment of the hour-glass interlocking nail of FIG. 6b wherein a plurality of fixation apertures is located throughout the mid section.

A method of using an hour-glass interlocking nail having an hour-glass geometry is provided. The method comprises the first step of examining a bone fracture to determine an appropriate sized hour-glass interlocking nail to be utilized. Appropriate length and diameter of the hour-glass interlocking nail is determined in selecting the hour-glass interlocking nail. The fractured bone has a bone canal with bone cortex interstitially therein. The method further comprises selecting the hour-glass interlocking nail. The hour-glass interlocking nail comprises a proximal section, mid section, and distal section. Each section of the hour-glass interlocking nail has a diameter and the proximal and distal sections each have a diameter larger than the mid section so that the hour-glass interlocking nail has an hour-glass geometry. At least one fixation aperture is located within either the proximal or distal section of the hour-glass interlocking nail. The proximal section comprises a proximal end having a connector adapted to be utilized for insertion and alignment of the hour-glass interlocking nail into the bone canal.

At least one locking means is selected. The locking means is appointed to be received by the fixation aperture located within either the proximal or distal section of the hour-glass interlocking nail. The locking means comprises a first end, center, and a second end. A substantial portion of the hour-glass interlocking nail is inserted into the bone canal. An alignment device is attached to the connector of the proximal end of the hour-glass interlocking nail. The bone is penetrated with the locking means, wherein the locking means enters the fixation aperture. The locking mean's first end extends from the hour-glass interlocking nail and traverses into the bone cortex, while the locking means center is housed within the fixation aperture and the second end of the locking means extends from the hour-glass interlocking nail and traverses into the bone cortex opposite the first end.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An hour-glass interlocking nail having a flexible, non-rigid geometry, comprising:
    a. a proximal section, a mid section, and a distal section, each of said sections of said interlocking nail having a diameter and said proximal and distal sections each having a diameter larger than the diameter of said mid section so that said interlocking nail has an hour-glass geometry; said proximal, mid and distal sections each having a solid cross-section, where said cross-sections are to be taken along a transverse plane through the proximal, mid and distal sections, aligned with the respective diameters of said sections; and said interlocking nail having a solid construct;
    b. the diameter of said interlocking nail gradually decreasing in size from said interlocking nail's proximal section to said interlocking nail's mid section;
    c. the diameter of said interlocking nail gradually increasing in size from said interlocking nail's mid section to said interlocking nail's distal section;
    d. said mid section having a first, second and central diameter creating a narrowed center point forming a smooth curve extending from said proximal and distal sections, said center point located at said mid section so that said proximal section and said distal section are virtually tapered cones increasing in diameter on both sides of said narrowed center point, wherein said interlocking nail is appointed to flex at said center point yielding said non-rigid geometry;
    e. at least one fixation aperture located within said proximal section, and at least one fixation aperture located within said distal section;
    f. said first and second diameter of said mid section being larger than said central diameter of said mid section;
    g. said proximal section comprises a proximal end, and said proximal end comprises a connector adapted to be utilized for insertion and alignment of said hour-glass interlocking nail into a bone canal; and
    h. the solid cross-section of said mid section being without slots or tubes therein and being adapted to flex when said hour-glass interlocking nail is inserted into a bone canal having a curved geometry.

2. An hour-glass interlocking nail as recited by claim 1, wherein said proximal and said distal sections of said hour-glass interlocking nail each have two said fixation apertures.

3. An hour-glass interlocking nail as recited by claim 1, wherein said fixation aperture has a first aperture diameter and a second aperture diameter, and said first aperture diameter is larger than said second aperture diameter so that said fixation aperture comprises a self-tapping, tapered, locking design.

4. An hour-glass interlocking nail as recited by claim 1, wherein said self-tapping, tapered, locking design of said fixation aperture is adapted to receive a screw-cone peg locking device.

5. An hour-glass interlocking nail as recited by claim 1, wherein said fixation aperture is adapted to receive a screw-cone peg, screw, bolt or peg.

6. An hour-glass interlocking nail as recited by claim 1, wherein said fixation aperture further comprises grooves therein and being adapted to engage with grooves on a screw-cone peg, screw, bolt, or peg.

7. An hour-glass interlocking nail as recited by claim 1, wherein said distal section comprises a distal tip, said distal tip having an arc therein constructed to form a tip having at least one arc portion.

8. An hour-glass interlocking nail as recited by claim 1, wherein said distal section comprises a distal tip having a substantially arced tip therein constructed to form a substantially radiused tip.

9. An hour-glass interlocking nail as recited by claim 1, wherein said distal section comprises a distal tip, and said distal tip has at least one flat edge to form a substantially sharp tip.

10. An hour-glass interlocking nail as recited by claim 1, wherein said connector further comprises at least one ridge portion, at least one cut-out portion, and a central aperture, and said central aperture extends through said proximal end and traverses into said proximal section.

11. An hour-glass interlocking nail as recited by claim 10, wherein said central aperture is threaded and adapted to receive a bit for insertion and alignment of said hour-glass interlocking nail into said bone canal.

12. An hour-glass interlocking nail as recited by claim 1, wherein said connector further comprises a conical fitting projecting therefrom said proximal end.

13. An hour-glass interlocking nail as recited by claim 12, wherein said conical fitting comprises at least one flat side for positioning and rotational control during insertion and alignment of said hour-glass interlocking nail.

14. An hour-glass interlocking nail as recited by claim 1, comprising a plurality of fixation apertures located within each of said mid, proximal and distal sections of said hour-glass interlocking nail.

\* \* \* \* \*